Figure 1:
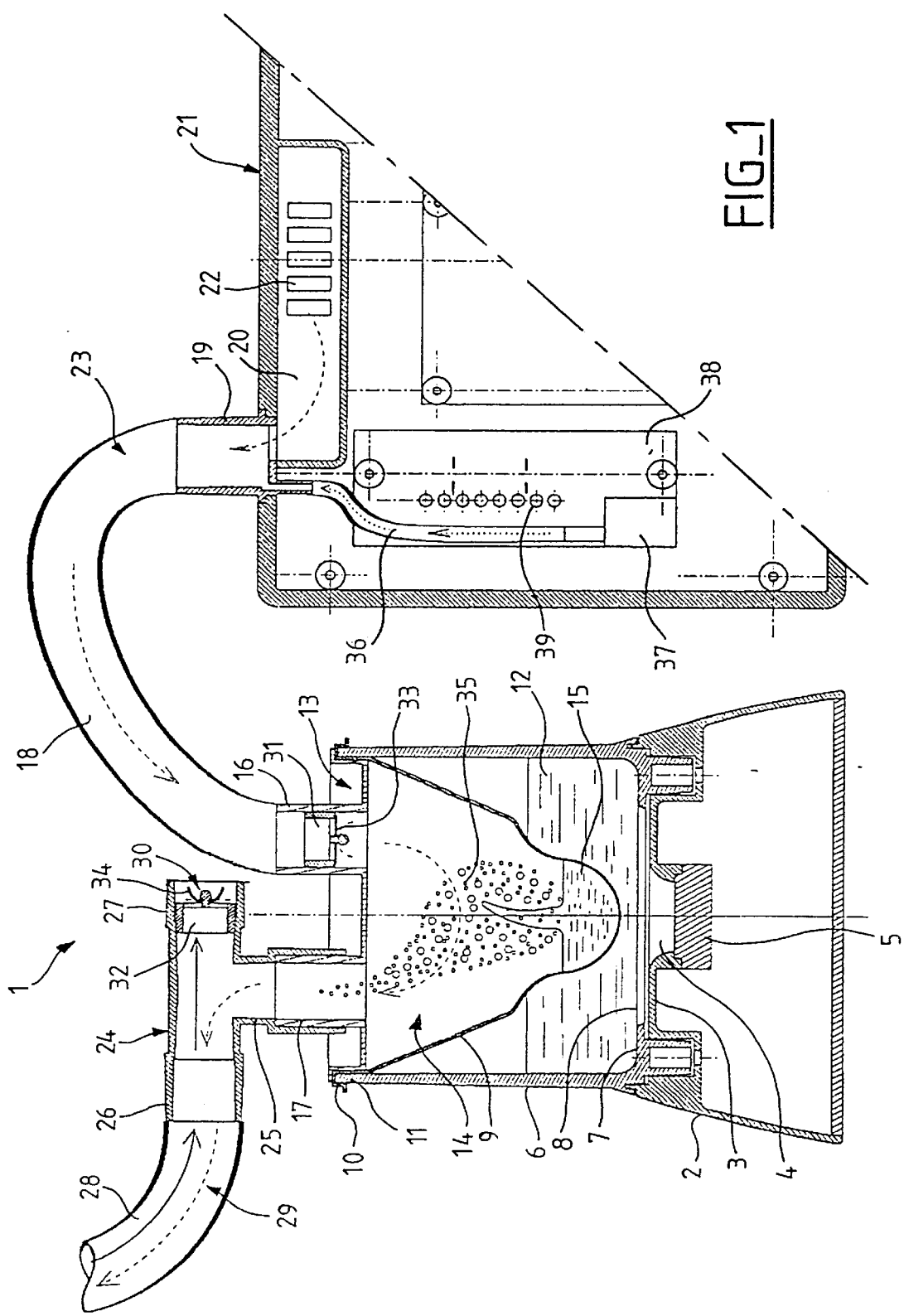

United States Patent [19]
Cinquin

[11] Patent Number: 5,865,171
[45] Date of Patent: Feb. 2, 1999

[54] NEBULIZER WITH PRESSURE SENSOR

[75] Inventor: Gérard Cinquin, Villeneuve-sur-Lot, France

[73] Assignee: System Assistance Medical, Villeneuve-sur-Lot, France

[21] Appl. No.: 826,792

[22] Filed: Mar. 24, 1997

[30] Foreign Application Priority Data

Mar. 26, 1996 [FR] France ................................ 96 03712
Aug. 22, 1996 [FR] France ................................ 96 12828

[51] Int. Cl.⁶ .............................................. A61M 15/00
[52] U.S. Cl. .............................. 128/203.12; 128/205.23; 128/200.14; 128/200.16; 128/202.22
[58] Field of Search ..................... 128/200.14, 200.16, 128/200.23, 202.13, 202.22, 205.23, 204.18; 340/611, 815.47; 482/13, 901; 600/538, 529

[56] References Cited

U.S. PATENT DOCUMENTS

| | | | |
|---|---|---|---|
| 3,828,773 | 8/1974 | Buch et al. | 128/200.16 |
| 4,001,650 | 1/1977 | Romain . | |
| 4,495,944 | 1/1985 | Brisson et al. | 128/205.23 |
| 4,635,647 | 1/1987 | Choksi . | |
| 5,063,922 | 11/1991 | Häkkinen | 128/200.16 |
| 5,099,833 | 3/1992 | Michaels | 128/200.16 |
| 5,167,506 | 12/1992 | Kilis et al. | 128/200.14 |
| 5,333,106 | 7/1994 | Lanpher et al. | 128/200.23 |
| 5,415,161 | 5/1995 | Ryder | 128/200.16 |
| 5,546,933 | 8/1996 | Rapoport et al. | 128/204.23 |

FOREIGN PATENT DOCUMENTS

| | | |
|---|---|---|
| 0667168 A | 8/1995 | European Pat. Off. . |
| 1095790 | 12/1967 | United Kingdom . |
| 2114064 | 8/1983 | United Kingdom . |
| WO-9103979 | 4/1991 | WIPO . |

OTHER PUBLICATIONS

Muschin W. William, et al. "Automatic Ventilation of the Lungs," 1980, Blackwell Scientific Publications, Oxford London Edinburgh Melbourne, XP002018916 166160, p. 452, 1. 13 –p. 453, 1. 4, p. 453, 11. 13–15, p. 455, 1. 17–19; figure 28.3.

*Primary Examiner*—John G. Weiss
*Assistant Examiner*—William J. Deane, Jr.
*Attorney, Agent, or Firm*—Beveridge, DeGrandi, Weilacher & Young, LLP

[57] ABSTRACT

A nebulizer includes an arrangement for forming a mist from a liquid and an arrangement for delivering the mist to a patient. The delivery arrangement includes an air circulation passage having an air inlet and an outlet to the patient, between which the mist that is formed is taken up by a current of air, together with an outlet to the open air. The nebulizer also has an inlet check valve in the air inlet, an outlet check valve in the outlet to the open air and an arrangement for sensing the pressure in the conveyor means, together with an arrangement for delivering an indication or warning signal depending on the value of the signal supplied by the pressure sensing arrangement and for determining at least one indication or warning signal level threshold.

11 Claims, 4 Drawing Sheets

FIG_2

NEBULIZER WITH PRESSURE SENSOR

BACKGROUND OF THE INVENTION

Field of the Invention

The present invention concerns a nebulizer for administering to a patent a mist for example containing a drug for treatment of their respiratory passages in particular.

The nebulizer of the invention includes means for forming a mist from a liquid and means for delivering this mist to a patient.

SUMMARY OF THE INVENTION

In accordance with the invention, said delivery means include an air circulation passage having an air inlet and an outlet to the patient between which the mist formed is taken up by a current of air, and also an outlet to the open air.

The nebulizer of the invention further includes an inlet check valve in said air inlet, an outlet check valve in said outlet to the open air, means for sensing the pressure in said delivery means and means for delivering an indication or warning signal according to the value of the signal supplied by said pressure sensing means and determining at least one indication or warning signal level threshold.

Accordingly, the patient can control the flowrate of the current of air produced in said circulation passage upon inhaling, by noting the amplitude or the value of said implication or warning signal relative to said signal level threshold corresponding to a particular reduction in pressure in said air circulation passage, thereby tending to inhale predetermined quantities of mist, depending in particular on said signal level threshold.

In one variant of the invention said delivery means include an air inlet conduit incorporating said inlet check valve, a chamber into which said inlet conduit discharges, a feed conduit for connecting said chamber to the patient and an outlet conduit to the open air connected to said feed conduit and incorporating said outlet check valve, the mist being formed in said chamber.

In accordance with the invention, said feed conduit preferably includes a T-shaped conduit a main branch of which is connected to said chamber, one of two other branches of which is connected to the patient and the other of the other two branches of which is connected to the open air, this branch connected to the open air incorporating said outlet check valve.

In another variant of the invention said delivery means include an air inlet conduit incorporating said inlet check valve, a feed conduit to the patient, an outlet conduit to the open air incorporating said outlet check valve, and an access conduit connected between said inlet conduit and said feed conduit and connected to a chamber in which the mist is formed.

In accordance with the invention, said outlet conduit to the open air is preferably connected to said feed conduit, downstream of the aforementioned connection of said access conduit.

In accordance with the invention, said pressure sensing means are preferably upstream of the inlet check valve of said inlet conduit.

In accordance with the invention, said pressure sensing means are preferably upstream of the aforementioned connection of said access conduit.

In accordance with the invention, said chamber may advantageously be formed in a tank closed by a lid to which said inlet and feed conduits are connected.

In accordance with the invention, said chamber may advantageously be formed in a tank provided with a lid to which said access conduit is connected.

In accordance with the invention, said pressure sensing means may advantageously include a pipe connected to said delivery means and at the end of which is a pressure sensor.

In accordance with the invention, the nebulizer preferably includes a cup disposed in a tank and closed by a lid to which said inlet and feed conduits are connected.

In accordance with the invention, said means for delivering an indication or warning signal may advantageously include two indication or warning signal level thresholds.

In accordance with the invention, said means for delivering an indication or warning signal may advantageously include visual means.

In accordance with the invention, said means for delivering an indication or warning signal may advantageously include light-emitting diodes of at least two colors for distinguishing said signal level threshold and means for selectively energizing said diodes according to the value of the signal supplied by said pressure sensing means.

In accordance with the invention, the level of the signal from said indication or warning means is preferably adjustable.

The present invention will be better understood from a study of a nebulizer described by way of nonlimiting example and shown in the accompanying drawings.

BRIEF DESCRIPTION OF THE DRAWINGS

FIG. 1 is a vertical sectional view of a nebulizer of the present invention.

FIG. 2 shows the block schematic of an electronic circuit for the above nebulizer.

FIG. 3 is a vertical sectional view of another nebulizer of the present invention.

FIG. 4 is a vertical sectional view of a further nebulizer of the present invention.

DETAILED DESCRIPTION OF THE PREFERRED EMBODIMENTS

FIG. 1 shows a nebulizer 1 having a base 2 which has a horizontal top wall 3 in the middle of which is a passage 4 to the bottom of which is fixed and sealed a quartz crystal vibrator 5.

The nebulizer 1 includes a cylindrical tank 6 which is mounted on the top wall 3 of the base 2 and the bottom 7 of which has an opening 8 communicating with the passage 4.

In the tank 6 is a cup 9 the rim 10 of which is supported by the rim 11 of the tank 6, the bottom part of the cup being at a distance from the top face of the quartz vibrator 5 and the tank 6 being partially filled with a liquid 12 such as water so that the bottom part of the cup 9 is immersed in the liquid 12.

A horizontal lid 13 is inserted in the top part of the cup 9 and with the latter delimits a nebulization chamber 14 in which a liquid 15 can be converted into a mist made up of fine droplets by the quartz vibrator 5.

The lid 13 has an upwardly projecting inlet pipe 16 and an upwardly projecting outlet pipe 17.

The inlet pipe 16 of the lid 13 is connected by a hose 18 to an outlet pipe 19 of a chamber 20 in an auxiliary unit 21, the chamber 20 being connected to the open air through openings 22 in its wall. The chamber 20, the pipe 19, the hose 18 and the pipe 16 constitute an inlet conduit 23 connecting the nebulization chamber 14 to the open air.

A T-shape pipe 24 is fitted to the outlet pipe 17 of the lid 13 with its main branch 25 supported by the pipe 17 and its opposite branches 26 and 27 respectively connected to a patient by a hose 28 and to the open air. The pipe 17, the T-shape pipe 24 and the hose 28 constitute a feed conduit 29 to which is connected an outlet conduit 30 formed by the branch 27 of the T-shape pipe 24.

The inlet pipe 16 of the lid 13 incorporates an inlet check valve 31 allowing air to flow only towards the nebulization chamber 14.

The branch 27 of the T-shape pipe 24 incorporates an outlet check valve 32 which allows air to flow only to the exterior.

In the example shown, the check valves 31 and 32 include radial elastic membranes 33 and 34 which, in a static position, respectively close off the conduits 23 and 30 and which, due to the effect of a current of air, are deformed elastically away from this position to allow the air to pass.

Accordingly, when the patient inhales via the free end of the feed conduit 28, the inlet check valve 31 is opened and the outlet check valve 32 is closed. The patient inhaling causes a current of air in the flow passage formed by the inlet conduit 23, the chamber 14 and the feed conduit 29 and the patient inhales the mist 35 that is formed continuously in the nebulization chamber 14 by the quartz vibrator 5.

On the other hand, when the patient exhales through the hose 28 the inlet check valve 31 is closed and the outlet check valve 32 is opened. The air exhaled by the patient passes to the exterior via the outlet conduit 30 to the open air. Because of the T-shape pipe 24, this exhalation expels to the exterior little or none of the mist 35 that continues to be formed in the nebulization chamber 14.

The nebulizer 1 further includes a hose 36 which opens laterally into the pipe 19 of the feed conduit 23 and has a small cross-section relative to that of the conduit 23, for example less than one tenth of the latter. The hose 36, which lies within the unit 21, is connected to a pressure sensor 37 carried by a printed circuit board 38. In this example, the board 38 also carries eight light-emitting diodes or LEDs 39 disposed one above the other and visible from the exterior of the unit 21.

FIG. 2 shows that the nebulizer 1 includes an electronic circuit, carried by the board 38, for example, which includes an amplifier 40 which receives the output signals from the pressure sensor 37 and which delivers amplified signals to a selector 41 which selectively energizes the light-emitting diodes 39.

The energization selector 41 successively and progressively turns on the light-emitting diodes 39 according to the value of the signals supplied by the pressure sensor 37, preferably in proportion to the reduction in pressure in the inlet conduit 23.

The selector 41 has an adjustment input 42 for adjusting a lower illumination value for which the first light-emitting diode is turned on and an adjustment input 43 for adjusting an upper illumination value for which the eighth light-emitting diode is turned on after the others are turned on in succession.

In one example, the two light-emitting diodes that are turned on first can be red, the next four green and the last two red. In this way the nebulizer 1 gives a visual indication of two signal level thresholds for the output signal of the sensor 37, located between the second and third diodes and between the sixth and seventh diodes.

When the patient is inhaling, as described above, the pressure drop that is established in the inlet conduit 23 is measured by the sensor 37 and the patient registers the magnitude of this pressure drop according to the number of light-emitting diodes 39 that are turned on.

By adjusting the selector 41 as required, using its adjustment inputs 42 and 43, a particular mode of inhalation can be imposed on the patient by instructing them to inhale in such a way that their inhalation turns on at least the first two light-emitting diodes without turning on the last two diodes.

By virtue of the foregoing arrangements, the nebulizer 1 provides a simple way of prescribing the patient predetermined quantities of mist 35 based approximately on an imposed flowrate of air in the inlet conduit 23. The quantities inhaled by the patient depend also on the duration of each inhalation, the time between inhalation and the adjustment of the quartz vibrator 5, which determines the quantity of mist that is formed continuously in the chamber 14.

FIG. 3 shows another nebulizer 44 which differs from the nebulizer 1 in terms of the means of forming a mist from a liquid and the means of delivering this mist to a patient.

The nebulizer 44 includes a tank 45 provided with a lid 46 which delimits a nebulization chamber 47. The bottom 48 of the tank 45 is provided with a central column 49 which extends upwards and has a central passage 50 connected below the bottom 48 to a pressurized air feed hose 51, the top end of the column 49 having an air outlet orifice 52.

A sleeve 53 fitted to the column 49 delimits a passage 54 that communicates with the bottom part of the tank 45, the top part of the sleeve 53 having an outlet orifice 55 facing and a small distance from the bottom end of a downwardly projecting part 60 of the lid 46.

Accordingly, air introduced via the bottom channel 50 of the column 49 aspirates liquid 61 introduced into the tank 45 and sprays it through the outlet orifice 55 of the sleeve 53 against the bottom end of the projecting part 60, this spraying forming a mist made up of very fine droplets of liquid.

The lid 46 has a vertical mouth 62 through which the mist that forms is evacuated.

The nebulizer 44 further includes a T-shape tubular member 63 with a central branch 64 and two opposite branches 65 and 66.

The central branch 64 is connected to the mouth 62 of the cover 46 to constitute an access conduit for the mist that is formed in the chamber 47. The branch 65 is divided in two in order to constitute an air inlet conduit 67 and an outlet conduit 68 to the open air, in the ends of which are mounted check valves 69 and 70 equivalent to the valves 31 and 32 of the previous example. The branch 66 constitutes a feed conduit to the end of which is connected a mouthpiece 71 which is adapted to be replaced by a hose connected to a remote mouthpiece.

Accordingly, when the patient inhales through the end of the mouthpiece 71 the inlet check valve 69 is opened and the outlet check valve 70 is closed. This inhalation by the patient causes a current of air in the flow passage formed by the inlet conduit 67, the feed conduit 66 and the mouthpiece 71, this current of air delivers to the patient the mist that is formed continuously in the chamber 47, entraining it as it enters the connection area of the access conduit 64.

On the other hand, when the patient exhales through the end of the mouthpiece 71 the inlet check valve 69 is closed and the outlet check valve 70 is opened. The air exhaled by the patient exits to the exterior via the outlet conduit 68 to the open air.

The nebulizer 44 further includes a hose 72 that opens laterally into the inlet conduit 67, downstream of the check valve 69, and which has a small cross-section relative to that of the conduit 67.

Figure 2:
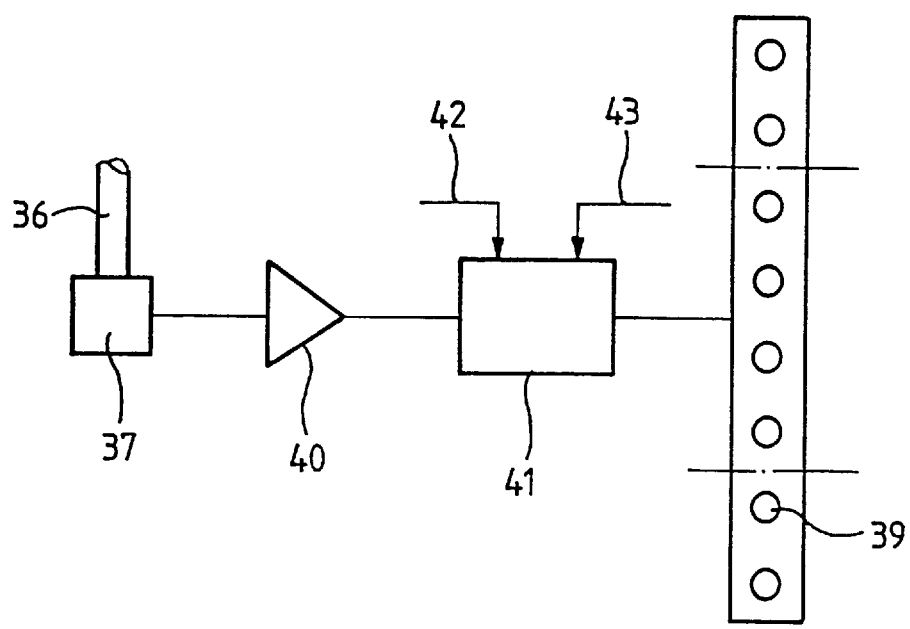

As in the previous example, this hose 72 constitutes a pressure sensor and is connected to an electronic unit 73 corresponding to the electronic 21 of the nebulizer described with reference to FIGS. 1 and 2, and operates in the same manner.

Figure 3:
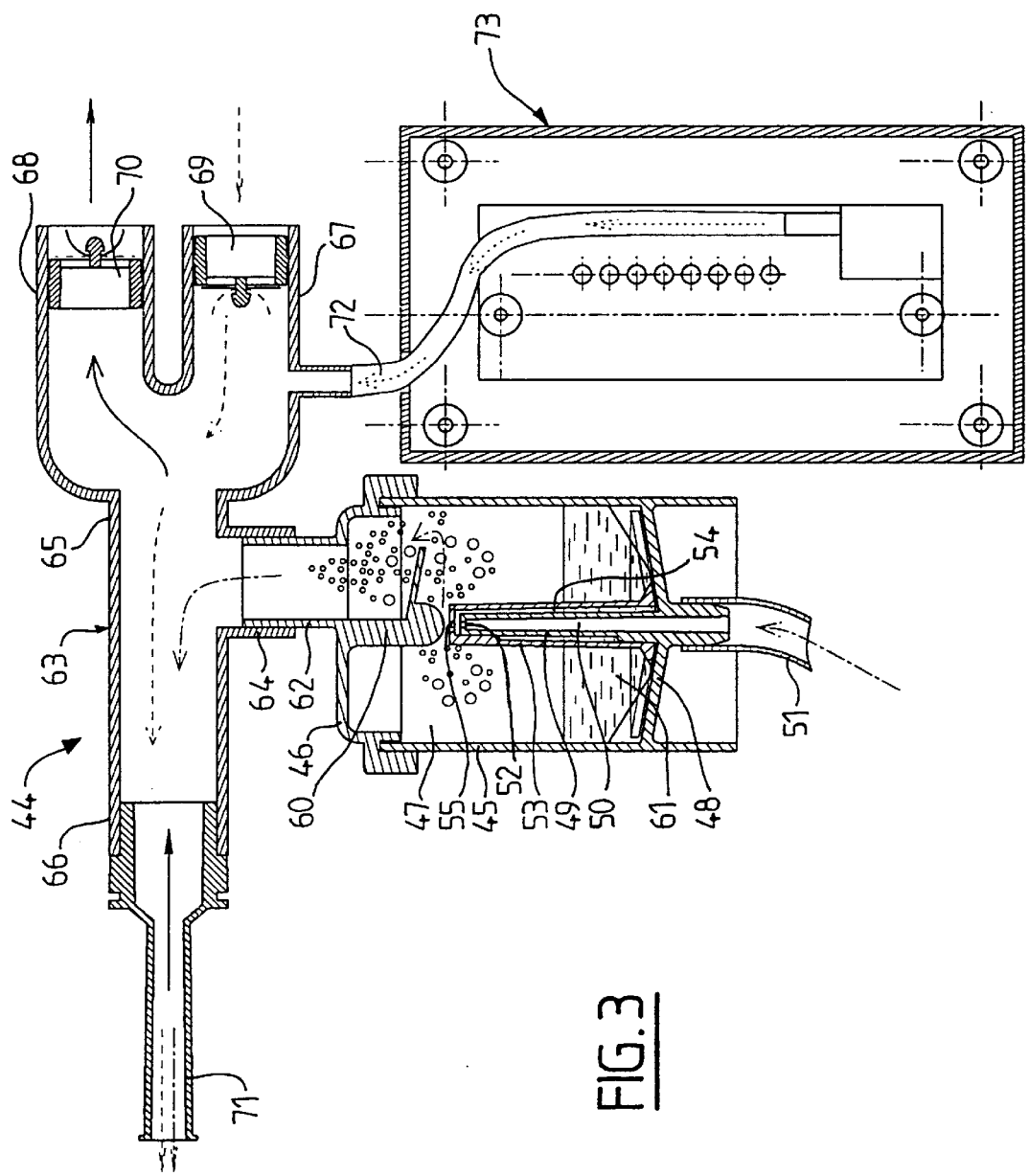
Figure 4:
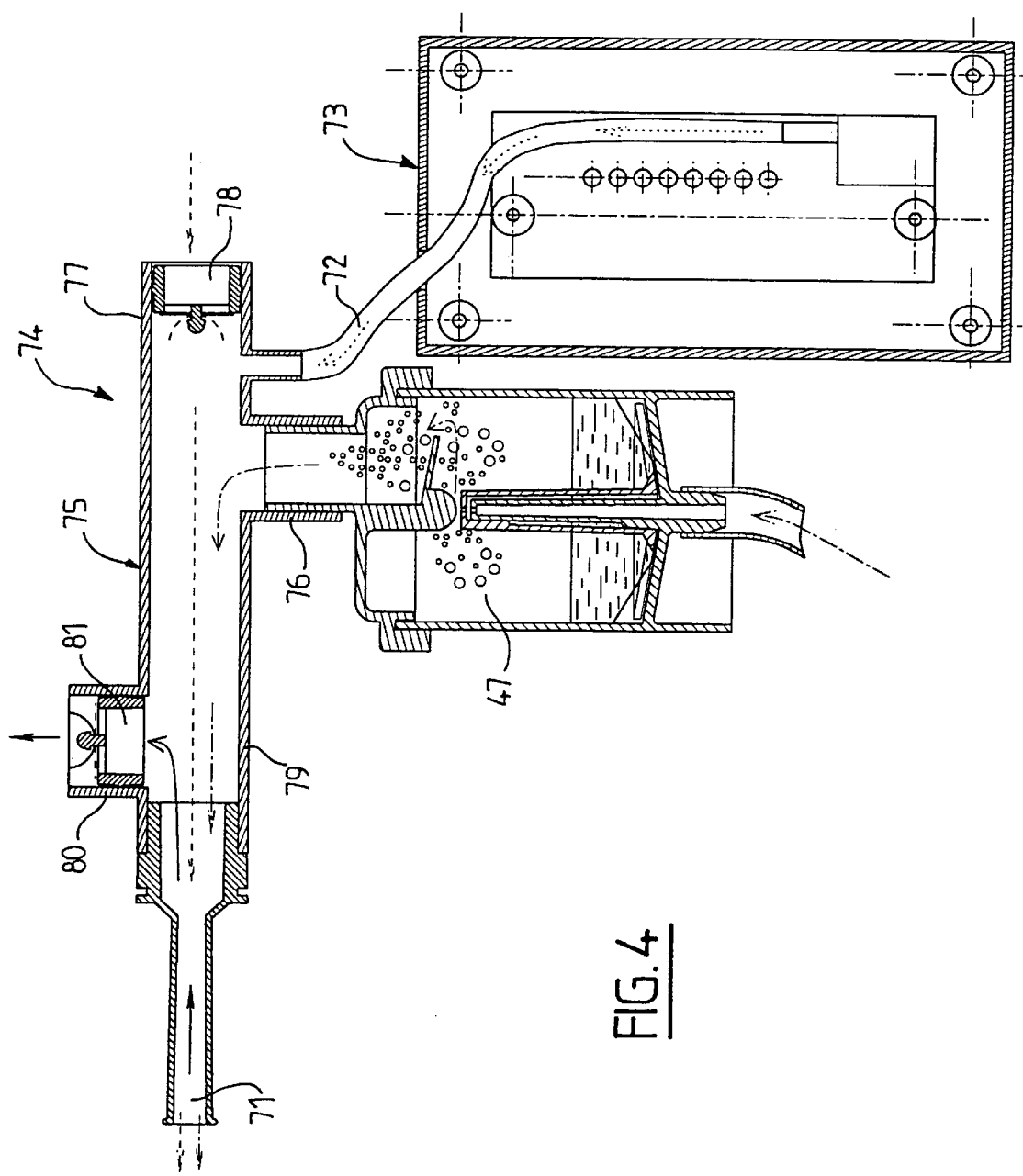

FIG. 4 shows a nebulizer 74 which constitutes a variant execution of the nebulizer 44 described with reference to FIG. 3, differing from the latter by its T-shape tubular member 75.

This tubular member 75 has a central branch 76 mounted on the pipe 62 in order to be connected to the nebulizer chamber 47 of the previous example and, opposite each other, an inlet conduit 77 in the end of which is disposed a check valve 78 and a feed conduit 79 to which is connected laterally, downstream of the connection area of the axis conduit 76, an exit conduit 80 to the free air in the end of which is disposed a check valve 81, the end of the branch 79 carrying the mouthpiece 71 of the previous example.

In this variant, when the patient exhales the exhaled current of air does not pass in front of the access conduit 76.

The pressure sensor hose 72 of the previous example is connected to the inlet conduit 77 downstream of the check valve 78 and upstream of the connection area of the access conduit 76 between the inlet conduit 77 and the feed conduit 79.

The present invention is not limited to the examples that have just been described. In particular, the pressure sensing means could be at a different location to the mist delivery means and the check valve could be of different construction. Moreover, the means of producing the mist could be different.

There is claimed:

1. A nebulizer, comprising:

a mist forming tank having a lid portion, said lid portion of said mist forming tank having separate inlet and outlet openings defined therethrough;

mist forming means, disposed inside said tank, for forming a mist from a liquid;

a T-shaped pipe member having a main branch and first and second opposite branches, said main branch of said T-shaped pipe member being in communication with said outlet opening of said lid;

a check valve operationally disposed in said first opposite branch of said T-shaped pipe member and arranged to prevent fluid flow into said T-shaped member through said first opposite branch;

a feed conduit engaged and in communication with said second opposite branch of said T-shaped pipe member;

an auxiliary unit having an outlet pipe defined therein, said outlet pipe comprising a main fluid intake orifice and a pressure sensing orifice, said main fluid intake orifice being in communication with a through opening to outside said auxiliary unit;

an inlet conduit engaged and in communication with said inlet opening of said lid and with said outlet pipe of said auxiliary unit;

a check valve positioned to prevent fluid from flowing out of said tank through said inlet opening;

means, supported by said auxiliary unit and in communication with said pressure sensing orifice of said outlet pipe, for determining a flow rate of fluid drawn into said feed conduit via, in succession, said through opening, said inlet conduit, said inlet opening, said mist forming tank, said outlet opening and second opposite branch and for generating a flow rate signal indicative thereof;

means for setting an upper flow rate threshold and a lower flow rate threshold; and displaying means, disposed on said auxiliary unit, for displaying a representation of said flow rate signal, said upper flow rate threshold and said lower flow rate threshold, wherein a patient using said nebulizer is directly informed of a flow rate in which said mist is inhaled and whether said flow rate is within preset upper and lower inhaling flow rate thresholds.

2. The nebulizer defined in claim 1, wherein:

said displaying means includes a visual displaying means for visually displaying said flow rate signal, said upper flow rate threshold and said lower flow rate threshold.

3. The nebulizer defined in claim 2, wherein:

said visual displaying means includes a plurality of light emitting diodes.

4. A nebulizer, comprising:

a mist forming tank having a lid portion and having a column supported by said tank and extending into an interior thereof, said lid portion of said tank having an outlet opening, said column defining an inner passage placing said interior of said tank in communication with outside said tank;

mist forming means, disposed inside said tank, for forming a mist from a liquid, said mist forming means including a sleeve engaged with said column and having an outlet orifice, a liquid feed passage defined between said sleeve and said column and communicating with said outlet orifice, and a downward projecting part supported by said tank and located in proximity to said outlet orifice;

a substantially T-shaped pipe member having a main branch and first and second opposite branches, said main branch of said substantially T-shaped pipe member being in communication with said outlet opening of said lid, said second opposite branch including separate inlet and outlet conduits, said inlet conduit containing a pressure sensing orifice;

an inlet check valve disposed in said inlet conduit and arranged to prevent fluid flow out of said substantially T-shaped pipe member through said inlet conduit;

an outlet check valve disposed in said outlet conduit and arranged to prevent fluid flow into said substantially T-shaped pipe member through said outlet conduit;

an auxiliary unit;

means, supported by said auxiliary unit and in communication with said pressure sensing orifice of said inlet conduit, for determining a flow rate of fluid drawn into said inlet conduit and for generating a flow rate signal indicative thereof;

means, supported by said auxiliary unit, for setting an upper flow rate threshold and a lower flow rate threshold; and displaying means, disposed on said auxiliary unit, for displaying a representation of said flow rate signal, said upper flow rate threshold and said lower flow rate threshold, wherein a patient using said nebulizer is directly informed of a flow rate in which said mist is inhaled and whether said flow rate is within preset upper and lower inhaling flow rate thresholds.

5. The nebulizer defined in claim 4, wherein:

said column extends outside said tank for engagement with a hose for delivery of high pressure air.

6. The nebulizer defined in claim 5, wherein:

said displaying means includes a visual displaying means for visually displaying said flow rate signal, said upper flow rate threshold and said lower flow rate threshold.

7. The nebulizer defined in claim 6, wherein:

said visual displaying means includes a plurality of light emitting diodes.

8. A nebulizer, comprising:

a mist forming tank having a lid portion and having a column supported by said tank and extending into an interior thereof, said lid portion of said tank having an outlet opening, said column defining an inner passage placing said interior of said tank in communication with outside said tank;

mist forming means, disposed inside said tank, for forming a mist from a liquid, said mist forming means including a sleeve engaged with said column and having a outlet orifice, a liquid feed passage defined between said sleeve and said column and communicating with said outlet orifice, and a downward projecting part supported by said tank in proximity to said outlet orifice;

a substantially T-shaped pipe member having a main branch and first and second opposite branches, said main branch of said substantially T-shaped pipe member being in communication with said outlet opening of said lid, said first branch including an inhalation opening and an outlet conduit defined in a side wall thereof, said second opposite branch including an inlet conduit, said inlet conduit containing a pressure sensing orifice;

an inlet check valve disposed in said inlet conduit and arranged to prevent fluid flow out of said substantially T-shaped pipe member through said inlet conduit;

an outlet check valve disposed in said outlet conduit and arranged to prevent fluid flow into said substantially T-shaped pipe member through said outlet conduit;

an auxiliary unit;

means, supported by said auxiliary unit and in communication with said pressure sensing orifice of said inlet conduit, for determining a flow rate of fluid drawn into said inlet conduit and for generating a flow rate signal indicative thereof;

means, supported by said auxiliary unit, for setting an upper flow rate threshold and a lower flow rate threshold; and displaying means, disposed on said auxiliary unit, for displaying a representation of said flow rate signal, said upper flow rate threshold and said lower flow rate threshold, wherein a patient using said nebulizer is directly informed of a flow rate in which said mist is inhaled and whether said flow rate is within preset upper and lower inhaling flow rate thresholds.

9. The nebulizer defined in claim 4, wherein:

said column extends outside said tank for engagement with a hose for delivery of high pressure air.

10. The nebulizer defined in claim 9, wherein:

said displaying means includes a visual displaying means for visually displaying said flow rate signal, said upper flow rate threshold and said lower flow rate threshold.

11. The nebulizer defined in claim 10, wherein:

said visual displaying means includes a plurality of light emitting diodes.

\* \* \* \* \*